United States Patent [19]
Peffly

[11] Patent Number: 5,980,876
[45] Date of Patent: Nov. 9, 1999

[54] HAIR SPRAY COMPOSITIONS

[75] Inventor: Majorie Mossman Peffly, Cincinnati, Ohio

[73] Assignee: The Procter & Gamble Company, Cincinnati, Ohio

[21] Appl. No.: 08/644,937

[22] Filed: May 13, 1996

Related U.S. Application Data

[63] Continuation of application No. 08/200,831, Feb. 17, 1994, abandoned, which is a continuation of application No. 07/883,979, May 15, 1992, abandoned, which is a continuation-in-part of application No. 07/747,165, Aug. 19, 1991, abandoned.

[51] Int. Cl.$^6$ .................................................... A61K 7/11
[52] U.S. Cl. ........................ 424/70.12; 424/45; 424/47; 424/70.2; 424/70.19; 424/70.22; 424/70.27; 424/70.31; 514/63
[58] Field of Search .................... 424/401, 70.2, 424/70.12, 70.121, 45, 47, 400, 70.1, 70.16, 70.17, 70.19, 70.22, 70.24, 70.27, 70.28, 70.31; 514/63; 528/10, 11, 31–35

[56] References Cited

U.S. PATENT DOCUMENTS

| | | | |
|---|---|---|---|
| 4,871,529 | 10/1989 | Sramek | 424/47 |
| 4,983,383 | 1/1991 | Maksimoski et al. | 424/70 |
| 5,021,477 | 6/1991 | Garbe et al. | 424/70 |
| 5,104,646 | 4/1992 | Bolich, Jr. et al. | 424/70 |
| 5,106,609 | 4/1992 | Bolich, Jr. et al. | 424/70 |

FOREIGN PATENT DOCUMENTS 0408311  1/1991  European Pat. Off. .

*Primary Examiner*—Neil S. Levy
*Attorney, Agent, or Firm*—Joan B. Tucker; Stephen T. Murphy; Leonard W. Lewis

[57] ABSTRACT

The present invention relates to hair spray compositions comprising from about 0.01% to about 2% of an ionic surfactant or a nonionic surfactant having an HLB of about 7 or less; from about 0.5% to about 15% of an ionic resin having a weight average molecular weight of at least about 300,000; and a liquid vehicle. This invention further relates to hairspray compositions comprising from about 0.5% to about 15% of an ionic, silicone macromer-containing resin as the hair setting agent, a liquid vehicle comprising a mixture of water and monohydric alcohol solvent (e.g., $C_1$–$C_3$ monohydric alcohols) wherein the composition contains at least about 10%, by weight of the composition, of water, and an ionic surfactant. Suitable surfactants are organic surfactant selected from the group consisting of anionic surfactants, amphoteric surfactants, zwitterionic surfactants, cationic surfactants, and nonionic surfactants having an average HLB of less than or equal to about 7.

20 Claims, No Drawings

HAIR SPRAY COMPOSITIONS

This is a continuation of application Ser. No. 08/200,831, filed on Feb. 17, 1994 now abandoned; which is a continuation of application Ser. No. 07/883,979, filed on May 15, 1992, now abandoned, which is a Continuation-In-Part of U.S. application Ser. No. 07/747,165, filed Aug. 19, 1991, now abandoned.

TECHNICAL FIELD

The present invention relates to hairspray compositions which exhibit good hair hold, as well as good spray characteristics.

BACKGROUND OF THE INVENTION

The desire to have the hair retain a particular shape is widely held. The most common methodology for accomplishing this is the application of a composition to dampened hair, after shampooing and/or conditioning, or to dry, styled hair. These compositions provide temporary setting benefits and they can be removed by water or by shampooing. The materials use in the compositions to provide the setting benefits have generally been resins and have been applied in the form of mousses, gels, lotions or sprays.

Many people desire a high level of style retention, or hold, from a hair spray composition. In typical hair sprays, hold is achieved by the use of resins, such as AMPHOMER®, supplied by National Starch and Chemical Co., and GANTREZ SP 225®, supplied by GAF Corp. These resins generally have a weight average molecular weight of from about 40,000 to about 150,000. When such resins are incorporated into pump and aerosol hair sprays, they provide hold and good sprayability. In general, as hair hold for hair spray compositions is increased, the tactile feel of the hair becomes stiffer and dense, less desirable. It is desirable to provide hair spray products which could provide an improved combination of hair hold and hair feel characteristics.

It has been found that the use of higher weight average molecular weight resins can be beneficial due to the increase in style retention generally expected to be provided by such resins and the general decrease in the amount of resin required for incorporation to achieve good style retention.

Unfortunately, the use of such higher molecular weight resins, such as those having a weight average molecular weight of greater than about 300,000, in aerosol and pump spray formulations has been difficult. Such formulations tend to exhibit poor spray quality. For example, they tend to have spray patterns characterized by wet drippy centers or to have spray characterized by streaming rather than a fine misting of hair spray particles. The difficulties in spraying higher molecular weight resins includes practical concerns, such as clogging, and also poor hair feel and hold. This is particularly a problem for silicone macromer-containing hair setting resins. Such hair setting agents are desirable for use because they can impart improved hair feel while still providing hair hold benefits. Such resins are also typically utilized at relatively high molecular weights relative to conventional, non-silicone macromer-containing resins.

It is an object of this invention to provide hairspray compositions which provide the benefits believed to be obtainable for high molecular weight resins without incurring the performance negatives that result from the difficulties in spraying such compositions.

Hair sprays have been conventionally formulated with high amounts of monohydric alcohol solvents, such as ethanol and isopropanol, and very low amounts of water, since the presence of water adversely affects spray quality. However, it remains desirable to formulate hair spray compositions with reduced levels of volatile organic solvents, such as ethanol and isopropanol. One way to do this, of course, is to increase the levels of water in the formulations, although this affects spray quality and performance.

It has recently been discovered that various silicone macromer-containing polymers, such as silicone macromer grafted copolymers, can be used to make hair spray compositions which combine hair styling (alternately, hair setting) with improved hair feel, e.g., softness relative to conventional hair styling polymers. These silicone macromer-containing polymers can be utilized at a wide variety of molecular weights. The lower molecular weight polymers, such as those from about 50,000 to 300,000 tend to be characterized by poor spray quality relative to conventional hair setting polymers. The higher molecular weight polymers are plagued with sprayability problems as previously discussed. These problems are especially prevalent for reduced volatile organic solvent formulations which contain relatively high levels of water. It is an additional object of this invention, to provide improved reduced volatile organic solvent hair spray products which can provide improved spray quality and performance.

SUMMARY OF THE INVENTION

The present invention relates to hair spray compositions comprising from about 0.01% to about 2% of an ionic surfactant or a nonionic surfactant having an HLB of about 7 or less; from about 0.5% to about 15% of an ionic resin having a weight average molecular weight of at least about 300,000; and a liquid vehicle. This invention further relates to hairspray compositions comprising from about 0.5% to about 15% of an ionic, silicone macromer-containing resin as the hair setting agent, a liquid vehicle comprising a mixture of water and monohydric alcohol solvent (e.g., $C_1$–$C_3$ monohydric alcohols) wherein the composition contains at least about 10%, by weight of the composition, of water, and an ionic surfactant, as described above. In particular, this invention relates to such a composition that is provided in a suitable means for containing and spraying the composition. Suitable surfactants are organic surfactants selected from the group consisting of anionic surfactants, amphoteric surfactants, zwitterionic surfactants, cationic surfactants, and nonionic surfactants having an average HLB of less than or equal to about 7.

Unless otherwise indicated, all percentages herein are by weight.

DETAILED DESCRIPTION OF THE INVENTION

The essential, as well as optional, components of the present invention are described below.

Surfactant

The hair spray compositions of the present invention contain, as an essential component, a surfactant. In general, the surfactant is present in the hair spray compositions in the range of from about 0.01% to about 2%, preferably from about 0.01% to about 1.5% and more preferably from about 0.02% to about 1%.

A wide variety of synthetic and natural organic surfactants are suitable for use in the hair spray compositions of the present invention. The term "organic surfactants" does not include fluorohydrocarbon surfactants, i.e., surfactants that are partially of fully fluorinated. Preferably, the organic surfactant is selected from the group consisting of anionic surfactants, amphoteric surfactants, zwitterionic surfactants, cationic surfactants, and nonionic surfactants having an average HLB of less than or equal to about 7, and mixtures thereof. More preferably, the organic surfactant is selected from the group consisting of anionic surfactants, zwitterionic surfactants and cationic surfactants. Mixtures of these surfactants may also be used.

Synthetic anionic surfactants useful herein include alkyl and alkyl ether sulfates. These materials have the respective formulae $ROSO_3M$ and $RO(C_2H_4O)H_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 1 to 20% by weight $C_{12-13}$ compounds; from 60 to 100% by weight of $C_{14-15-16}$ compounds, from about 1 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from 0.1 to 15% by weight of compounds having a degree of ethoxylation greater than 8.

Another suitable class of anionic surfactants are the water-soluble salts of the organic, sulfuric acid reaction products of the general formula: $R_1$—$SO_3$—M wherein $R_1$ is chosen from the group consisting of a straight or branched chain, saturated aliphatic organic radical having from 8 to 24, preferably 12 to 18, carbon atoms; and M is a cation. Important examples are the salts of an organic sulfuric acid reaction product of a organic of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Additional examples of anionic synthetic surfactants which come within the terms of the present invention are the reaction product of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic detergents of this variety are set forth in U.S. Pat. Nos. 2,486,921; 2,486,922; and 2,396,278.

Still other anionic synthetic surfactants include the class designated as succinamates. This class includes such surface active agents as sulfosuccinamates, eg. disodium N-octadecyl-sulfosuccinamate, tetrasodium N-(1,2-dicarboxyethyl)-N-octadecylsulfosuccinamate, diamyl ester of sodium sulfosuccinic acid, dihexyl ester of sodium sulfosuccinic acid, and dioctyl esters of sodium sulfosuccinic acid.

Suitable anionic surfactants utilizable herein include olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated organics, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued Jul. 25, 1967, titled "Detergent Composition", the disclosure of which is incorporated herein by reference.

Another class of anionic organic surfactants are the β-alkyloxy alkane sulfonates. These compounds have the following formula:

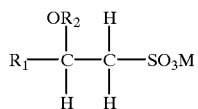

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include: potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecysulfonate, and ammonium β-n-propoxy-dodecylsulfonate.

Many additional nonsoap synthetic anionic organic surfactants are described in McCUTCHEON'S DETERGENTS AND EMULSIFIERS, 1984 ANNUAL, published by Allured Publishing Corporation, which is incorporated herein by reference. Also U.S. Pat. No. 3,929,678, Dec. 30, 1975 to Laughlin et al. discloses many other anionic as well as other surfactant types and is incorporated herein by reference.

Particularly preferred anionic surfactants for use are alkyl ethoxylated sulfates and alkyl sulfates such as ammonium and sodium salts of laureth sulfate and laureth sulfate, ammonium lauryl and sulfate. Another preferred type of surfactant for use in the present invention are dioctyl esters of sodium sulfosuccinic acid.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Preferred amphoteric surfactants for use are alkyl, preferably $C_6$–$C_{22}$ and most preferably $C_8$–$C_{12}$, amphoglycinates; alkyl, preferably $C_6$–$C_{22}$ and most preferably $C_8$–$C_{12}$, amphopropionates; and mixtures thereof. Particularly, cocoamphoglycinate, lauroamphocarboxyglycinate, isostearoamphopropionate, cocoamphocarboxypropionic acid, cocoamphocarboxyglycinate, and mixtures thereof are preferred. The most preferred cocoamphocarboxyglycinate for use is supplied as Monateric 805 by Mona Industries.

Suitable zwitterionic surfactants for use in the present compositions can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

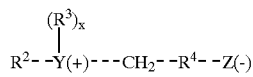

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is sulfur or phosphorus, or 1 or 2 when Y is nitrogen; $R^4$ is an alkylene or hydroxyalkylene of from 1 to about 4 carbon atoms and Z is a radical selected from the group consisting of carboxylate, sulfonate, sulfate, phosphonate, and phosphate groups. Classes of zwitterionics include alkyl amino sulfonates, alkyl betaines, and alkyl amido betaines.

Examples include: 4-[N,N-di(2-hydroxyethyl)-N-octadecylammonio]-butane-1-carboxylate; 5-[S-3-hydroxypropyl-S-hexadecylsulfonio]-3-hydroxy-pentanel-sulfate; 3-[P,P-diethyl-P-3,6,9-trioxatetradexoxylphosphonio]-2-hydroxy-propane-1-phosphate; 3-[N,N-dipropyl-N-3-dodecoxy-2-hydroxypropylammonio]-propane-1-phosphate; 3-(N,N-dimethyl-N--hexadecylammonio)propane-1-sulfonate; 3-(N,N-dimethyl-N-hexadecylammonio)-2-hydroxy-propane-1-sulfonate; 4-[N,N-di-(2-hydroxy-ethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and 5-[N,N-di(3-hydroxypropyl)-N-hexadecylammonio]-2-hydroxypentane-1-sulfate.

A preferred zwitterionic is cocoamphopropyl sulfonate.

Other zwitterionic betaines are useful in the present invention. Examples of alkyl betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxy methyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis(2-hydroxyethyl) sulfopropyl betaine and the like; alkyl amido betaines and amidosulfobetaines, wherein the $R_x$CONH $(CH_2)$ radical (x is preferably from 1 to 6) is attached to the nitrogen atom of the betaine are also useful. The alkyl betaines and alkyl amido betaines are preferred for use in the compositions of the present invention.

A preferred alkyl betaine for use in the present hair spray compositions is the coco-betaine supplied as Monateric CB by Mona Industries. A preferred alkyl amido betaine for use in the present hair spray compositions is cocoamidopropyl betaine. Zwitterionic surfactants also include, for example, sodium 3-dodecylaminopropane sulfonate; alkyl, preferably $C_6$–$C_{22}$ and most preferably $C_8$–$C_{12}$, amphosulfonates; alkyl, preferably $C_6$–$C_{22}$ and most preferably $C_8$–$C_{12}$, amphosulfosuccinates; oleoamphopropylsulfonate, and cocoamphopropylsulfonate.

Cationic surfactants useful in compositions of the present invention contain amino or quaternary ammonium hydrophilic moieties which are positively charged when dissolved in the aqueous composition of the present invention. Cationic surfactant vehicle materials among those useful herein are disclosed in the following documents, all incorporated by reference herein: M. C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

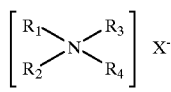

wherein R₁ is an aliphatic group of from 1 to 22 carbon atoms, or an aromatic, aryl or alkylaryl group having from 12 to 22 carbon atoms; R₂ is an aliphatic group having from 1 to 22 carbon atoms; R₃ and R₄ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups.

Other quaternary ammonium salts useful herein are diquaternary ammonium salts, such as tallow propane diammonium dichloride.

Exemplary quaternary ammonium salts include dialkyldimethylammonium chlorides, wherein in the alkyl groups have from 12 to 22 carbon atoms and are derived from long-chain fatty acids, such as hydrogenated tallow fatty acid. (Tallow fatty acids give rise to quaternary compounds wherein R₁ and R₂ have predominately from 16 to 18 carbon atoms.) Such quaternary ammonium salts include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, and di(coconutalkyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di(hydrogenated tallow) dimethyl ammonium chloride is a particularly preferred quaternary ammonium salt.

Salts of primary, secondary and tertiary fatty amines are also contemplated. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine hydrochloride, stearylamine formate and N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981 (incorporated by reference herein).

Nonionic surfactants having an average HLB (Hydrophile-Lipophile Balance) of less than or equal to about 7 can be used in the present hair spray compositions. Blends of nonionic organic surfactants containing nonionic organic surfactants with a HLB of greater than 7 are suitable for use in the present compositions as long as the average HLB of the blends is less than or equal to about 7.

The HLB System was introduced in the late 1940's by ICI Americas Inc. Methods of determining HLB are well known in the art and any of such methods may be used for HLB determination. A description of the HLB System and methods for HLB determination are described in "The HLB System: a time saving guide to emulsifier selection," ICI Americas Inc.; Wilmington, Del.; 1976.

Nonionic surfactants suitable for use herein can be broadly defined as compounds containing a hydrophobic moiety and a nonionic hydrophilic moiety. Examples of the hydrophobic moiety can be alkyl, alkyl aromatic, dialkyl siloxane, and polyoxyalkylene alkyls. Examples of hydrophilic moieties are polyoxyalkylenes, phosphine oxides, sulfoxides, amine oxides, and amides. Examples of preferred classes of nonionic organic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 1 to about 6 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 10% to about 40% polyoxyethylene by weight and having a molecular weight of from about 500 to about 4,000 resulting from the reaction of ethylene oxide groups with a hydrophobic base constituted of the reaction product of ethylene diamine and excess propylene oxide, said base having a molecular weight of the order of about 2,500 to about 10,000, are satisfactory.

3. The condensation product of aliphatic alcohols having from about 8 to about 20 carbon atoms, in either straight chain or branched chain configuration, with ethylene oxide, e.g., a tallow alcohol ethylene oxide condensate having from about 2 to about 10 moles of ethylene oxide per mole of tallow alcohol, the tallow alcohol fraction having from about 16 to about 18 carbon atoms.

4. Long chain tertiary amine oxides corresponding to the following general formula:

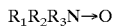

wherein R₁ contains an alkyl, alkenyl or monohydroxy alkyl radical of from about 12 to about 22 carbon atoms, from 0 to about 10 ethylene oxide moieties, and from 0 to about 1 glyceryl moiety, and R₂ and R₃ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyloctadecylamine oxide, oleyldi(methyl) amine oxide, dimethylhexadecylamine oxide, behenyldimethylamine oxide.

5. Long chain tertiary phosphine oxides corresponding to the following general formula:

wherein R contains an alkyl, alkenyl or monohydroxyalkyl radical ranging from about 12 to about 22 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 12 to about 20 carbon atoms, from 0 to about 10 ethylene oxide moieties and from 0 to about 1 glyceryl moiety.

7. Silicone copolyols such as the dimethicone copolyols. Among those useful herein are those disclosed in the following patent documents, all incorporated by reference herein: U.S. Pat. No. 4,122,029, Gee, et al., issued Oct. 24, 1978; U.S. Pat. No. 4,265,878, Keil, issued May 5, 1981; and U.S. Pat. No. 4,421,769, Dixon, et al., issued Dec. 20, 1983. Such dimethicone copolyol materials are also disclosed, in hair compositions, in British Patent Application 2,066,659, Abe, published Jul. 15, 1981 (incorporated by reference herein) and Canadian Patent 727,588, Kuehns, issued Feb. 8, 1966 (incorporated by reference herein). Commercially available dimethicone copolyols which can be used herein, include Silwet Surface Active Copolymers (manufactured by the Union Carbide Corporation); and Dow Corning Silicone Surfactants (manufactured by the Dow Corning Corporation).

8. Amide surfactants which include the ammonia, monoethanol, diethanol, and other alkanol amides of fatty acids having an acyl moiety of from about 8 to about 22 carbon atoms and represented by the general formula:

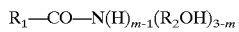

$$R_1-CO-N(H)_{m-1}(R_2OH)_{3-m}$$

wherein $R_1$ is a saturated or unsaturated, aliphatic hydrocarbon radical having from 7 to 21, preferably from 11 to 17 carbon atoms; $R_2$ represents a $C_{1-4}$ alkylene group; and m is 1, 2 or 3, preferably 1. Specific examples of said amides are mono-ethanol coconut fatty acids amide and diethanol dodecyl fatty acid amide. These acyl moieties may be derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process. The monoethanol amides and diethanolamides of $C_{18-22}$ fatty acids are preferred.

Examples of preferred nonionic surfactants for use herein are stearamide diethanolamide (DEA), cocamide monoethanolamide (MEA), glyceryl monoleate, sucrose stearate, Cetheth-2, Poloxamer 181, and hydrogenated tallow amide DEA.

Examples of other suitable nonionic surfactants supplied by ICI Americas are polyoxyethylene 4 sorbitol beeswax derivative (ATLAS 6-1702), polyoxyethylene 2 cetyl ether (BRIJ 52), polyoxyethylene 2 stearyl ether (BRIJ 72), polyoxyethylene 2 oleyl ether (BRIJ 92), polyoxyethylene 2 oleyl ether (BRIJ 93), sorbitan monopalmitate (SPAN 40), sorbitan monostearate (SPAN 60), sorbitan tristearate (SPAN 65), sorbitan monoleate, NF (SPAN 80) and sorbitan trioleate (SPAN 85).

Many additional surfactants are described in MCCUTCHEON'S DETERGENTS AND EMULSIFIERS, 1979 ANNUAL, published by Allured Publishing Corporation, which is incorporated herein by reference.

Resin

As used herein, "ionic resin" means any ionic polymer or copolymers, natural or synthetic, that can provide hair setting benefits. Resins of this type are well known in the art. Generally, the level of hair styling polymer used will be at least about 0.1%, by weight, of the composition. Typically, it will be present at a level of from about 0.1% to about 15%, preferably from about 0.5% to about 8%, more preferably front about 1% to about 5%.

As used herein, "ionic" or "ionic character" in reference to polymers or monomers of which such polymers are comprised, refers to materials which contain anionic, cationic, amphoteric, zwitterionic, or other groups that can exist in the liquid vehicle of the hair styling composition in dissociated ionic form.

Any type of ionic polymer which is soluble or dispersible in the liquid carrier can be used in the present invention. A wide variety of such types of polymers are known in the art.

The ionic polymers hereof can be homopolymers, copolymers, terpolymers, etc. As used herein, the term "polymer" shall encompass all of such types of polymeric materials.

As an essential aspect, the resins hereof must comprise monomers of an ionic character. For convenience in describing the polymers hereof, monomeric units present in the polymers may be referred to as the monomers from which they can be derived. The ionic monomers can be derived from polymerizable ionic starting monomers, or from polymerizable nonionic monomers which are modified subsequent to polymerization to be of ionic character. Also included are corresponding salts, acids, or bases of the monomers exemplified.

Examples of anionic monomers include:

(i) unsaturated carboxylic acid monomers such as acrylic acid, methacrylic acid, maleic acid, maleic acid half ester, itaconic acid, fumaric acid, and crotonic acid;

(ii) half esters of an unsaturated polybasic acid anhydride such as succinic anhydride, phthalic anhydride or the like reacted with a hydroxyl group-containing acrylate and/or methacrylate such as hydroxyethyl acrylate and hydroxyethyl methacrylate, hydroxypropyl acrylate and the like;

(iii) monomers having a sulfonic acid group such as styrenesulfonic acid, sulfoethyl acrylate and methacrylate, and the like; and (iv) monomers having a phosphoric acid group such as acid phosphooxyethyl acrylate and methacrylate, 3-chloro-2-acid phosphooxypropyl acrylate and methacrylate, and the like.

Examples of the cationic monomers include:

(i) monomers derived from acrylic acid or methacrylic acid, which is referred to hereinafter collectively as (meth)acrylic acid, and a quaternarized epihalohydrin product of a trialkylamine having 1 to 5 carbon atoms in the alkyl such as (meth)acryloxypropyltrimethylammonium chloride and (meth)acryloxypropyltriethylammonium bromide;

(ii) amine derivatives of (meth)acrylic acid or amine derivatives of (meth)acrylamide derived from (meth) acrylic acid or (meth)acrylamide and a dialkylalkanolamine having $C_1$–$C_4$ alkyl groups such as dimethylaminoethyl (meth)acrylate, diethylaminoethyl (meth)acrylate, dimethylaminopropyl (meth)acrylate, or dimethylaminopropyl (meth)acrylamide; and (iii) derivatives of the products of the group (ii) above by (1) neutralization with an acid such as hydrochloric acid, or lactic acid, (2) modification with a halogenated alkyl, such as methyl chloride, ethyl chloride, methyl bromide, or ethyl iodide, (3) modification with a halogenated fatty acid ester such as ethyl monochloroacetate, or methyl monochloropropionate, and (4) modification with a dialkyl sulfate such as dimethyl sulfate, or diethyl sulfate.

Furthermore, the cationic unsaturated monomers include amine derivatives of allyl compounds such as diallyldimethylammonium chloride and the like.

These cationic unsaturated monomers can be polymerized in cationic form, or as an alternative they can be polymerized in the form of their precursors, which are then modified to be cationic, for example, by a quaternizing agent (e.g. ethyl monochloroacetate, dimethyl sulfate, etc.).

Examples of the amphoteric monomers include zwitterionized derivatives of the aforementioned amine derivatives of (meth)acrylic acids or the amine derivatives of (meth)acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

These amphoteric monomers, like the aforementioned cationic monomers, can be polymerized in amphoteric form or, as an alternative, they can also be polymerized in the form of their precursors, which are then converted into the amphoteric state.

Preferred ionic monomers include acrylic acid, methacrylic acid, dimethylaminoethyl methacrylate, quaternized dimethylaminoethyl methacrylate, maleic acid, maleic anhydride half esters, crotonic acid, itaconic acid, diallyldimethyl ammonium chloride, polar vinyl heterocyclics such as vinyl imidazole, vinyl pyridine, styrene sulfonate, salts of the acids and amines described above (e.g., alkali and alkaline earth metal salts such as sodium and potassium), and mixtures thereof. Especially preferred ionic monomers include acrylic acid, dimethylaminoethyl methacrylate, quaternized dimethylaminoethyl methacrylate, and salts and mixtures thereof.

The polymers hereof should contain at least about 1%, by weight, ionic monomer, preferably at least about 2%, more preferably at least about 5%.

The resins hereof can also contain nonionic monomers including, both high polarity monomers and low polarity monomers.

The ionic resins hereof will generally comprise from about 1% to 100% ionic monomers and from 0% to about 99% nonionic monomers, preferably from about 2% to about 75% ionic monomers and from about 25% to about 98% nonionic monomers, more preferably from about 5% to about 50% ionic monomers and from about 50% to about 95% nonionic monomers.

Representative examples nonionic monomers are acrylic or methacrylic acid esters of $C_1$–$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri-methyl-1-hexanol, 1-decanol, 1-dodecanol, 1-hexadecanol, 1-octa-decanol, and the like, the alcohols having from about 1–24 carbon atoms with the average number of carbon atoms preferably being from about 4–18, more preferably from about 4–12; styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, such as methoxy ethyl (meth)acrylate and butoxyethyl (meth)acrylate; and mixtures thereof. Other nonionic monomers include acrylate and methacrylate derivatives such as allyl acrylate and methacrylate, cyclohexyl acrylate and methacrylate, and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, and the like.

Preferred nonionic monomers include n-butyl methacrylate, isobutyl methacrylate, 2-ethylhexyl methacrylate, methyl methacrylate, t-butylacrylate, t-butylmethacrylate, and mixtures thereof.

Representative polar nonionic monomers include acrylamide, N,N-dimethylacrylamide, methacrylamide, N-t-butyl acrylamide, methacrylonitrile, acrylamide, acrylate alcohols (e.g. $C_2$–$C_6$ acrylate alcohols such as hydroxyethyl acrylate, hydroxyproxyl acrylate), hydroxyethyl methacrylate, hydroxypropyl methacrylate, vinyl pyrrolidone, vinyl ethers, such as methyl vinyl ether, acyl lactones and vinyl pyridine, allyl alcohols, vinyl alcohols and vinyl caprolactam.

Examples of anionic hair spray resins are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride (molar ratio about 1:1) wherein such copolymers are 50% esterified with a saturated aliphatic alcohol containing from 1 to 4 carbon atoms such as ethanol or butanol; and acrylic copolymers and terpolymers containing acrylic acid or methacrylic acid as the anionic radical containing moiety such as copolymers with methacrylic acid, butyl acrylate, ethyl methacrylate, etc. Another example of an acrylic polymer which can be employed in the compositions of the present invention is a polymer of tertiary-butyl acrylamide, acrylic acid, and ethyl acrylate.

An example of an amphoteric resin which can be used in the present invention is Octylacrylamide/Acrylates/Butylaminoethyl Methacrylate Copolymer, described generally in U.S. Pat. No. 4,192,861 as being a polymer of N-tert-octyl acrylamide, methyl methacrylate, hydroxypropyl methacrylate, acrylic acid and t-butyl aminoethyl methacrylate, of appropriate molecular weight for purposes hereof.

Examples of cationic hair spray resins are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

Still other organic, ionic resins include carboxymethyl cellulose, copolymers of PVA and crotonic acid, copolymers of PVA and maleic anhydride, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether-maleic acid), and octylacrylamide/ acrylate/butylaminoethyl methacrylate copolymers. Mixtures of polymers may also be used.

Preferred ionic resins include silicone-containing ionic polymers. Silicone-containing ionic polymers are described, for example, in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, U.S. Ser. No. 07/758,319, Bolich et al, filed Aug. 27, 1991, and U.S. Ser. No. 07/758,320, Torgerson et al., filed Aug. 27, 1991, all of which are incorporated by reference herein.

Preferred silicone-containing ionic polymers contain an organic polymeric backbone, preferably a vinyl backbone, having a Tg above about $-20°$ C. and, grafted to the backbone, a siloxane macromer having a weight average molecular weight of preferably at least about 500, more preferably from about 1,000 to about 100,000, even more preferably from about 2,000 to about 50,000, most preferably about 5,000 to about 20,000. In addition to the graft copolymers described above, silicone-containing polymers also include block copolymers preferably containing up to about 50% (more preferably from about 10% to about 40%) by weight of one or more siloxane blocks and one or more non-silicone blocks (such as acrylates or vinyls).

The silicone-containing ionic polymers preferred for use herein are such that when formulated into the finished hair care composition, and dried, the polymer phase separates into a discontinuous phase which includes the silicone portion and a continuous phase which includes the organic portion.

The silicone-containing ionic polymers generally comprise nonionic silicone-containing monomers together with ionic monomers as described above, and can also contain non-silicone-containing nonionic monomers, also described above. The silicone-containing monomers also can be tonically charged and, as such, contribute, in part or in whole, to the overall charge density of the polymer.

Examples of useful silicone-containing ionic polymers and how they are made are described in detail in U.S. Pat. No. 4,693,935, Mazurek, issued Sep. 15, 1987, and U.S. Pat. No. 4,728,571, Clemens et al., issued Mar. 1, 1988, both of which are incorporated herein by reference.

The silicone-containing ionic polymers hereof will generally comprise about 0.01% to about 50% of silicone-containing monomer, preferably from about 0.5% to about 40% of ionic monomer, more preferably from about 2% to about 25%.

The silicone-containing monomer has the general formula:

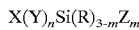

wherein X is a vinyl group copolymerizable with the other monomers of the polymer; Y is a divalent linking group; R is a hydrogen, hydroxyl, lower alkyl (eg., $C_1$—$C_4$), aryl, alkylamino, alkaryl, or alkoxy; Z is a monovalent siloxane polymeric moiety having a number average molecular weight of at least about 500, and is pendant from the organic polymeric backbone, described above; n is 0 or 1; and m is an integer from 1 to 3. Of course, Z should be essentially unreactive under polymerization conditions. The silicone-containing monomer preferably has a weight average molecular weight of at least about 500 to preferably from about 1,000 to about 100,000 more preferably from about 2,000 to about 50,000, most preferably from about 5,000 to about 20,000. Preferably, it is of a formula as follows:

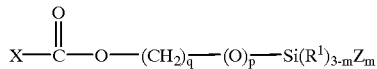

In the above structure, m is 1, 2 or 3 (preferably m=1); p is 0 or 1; $R^1$ is alkyl, aryl, alkaryl, alkoxy, alkylamino, hydroxyl, or hydrogen, preferably alkyl or hydrogen; q is an integer from 2 to 6; s is an integer from 0 to 2; X is

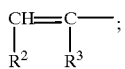

$R^1$ is hydrogen or —COOH (preferably $R^2$ is hydrogen); $R^3$ is hydrogen, methyl or —$CH_2COOH$ (preferably $R^3$ is methyl); Z is

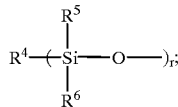

$R^4$, $R^5$, $R^6$ independently are alkyl, alkoxy, alkylamino, aryl, alkaryl, hydrogen or hydroxyl (preferably alkyl, more preferably methyl); and r is an integer of at least about 5, preferably from about 10 to about 1500 (more preferably from about 75 to about 700, most preferably from about 100 to about 250). Particularly preferred is when p=0 and q=3, $R^2$ is hydrogen or —COOH (preferably $R^2$ is hydrogen); and $R^3$ is hydrogen, methyl or —$CH_2COOH$ (preferably $R^3$ is methyl).

The silicone-containing monomers of the ionic polymers hereof can be polymerized in a silicone-containing monomer form. Alternatively, they can be polymerized in the form of their non-silicone containing precursor, and a silicone group can then be added. For example, carboxylate-containing monomers, such as acrylic acid, can be polymerized and then reacted with a silicone-containing compound with a terminal epoxy group. The result will, in general, be a silicone-containing monomer in the polymer having an equivalent structure to the formula $X(Y)_nSi(R)_{3-m}Z_m$, described above, and is intended to be encompassed herein.

The preferred silicone-containing ionic polymers useful in the present invention generally comprise from 0% to about 98% (preferably from about 5% to about 98%, more preferably from about 50% to about 90%) of nonionic monomer, from 1% to about 98% (preferably from about 15% to about 80%) of ionic monomer, with from about 0.1% to about 50% (preferably from about 0.5% to about 40%, most preferably from about 2% to about 25%) of the monomers being silicone-containing monomer. The combination of the non-silicone-containing monomers preferably is from about 50% to about 99% (more preferably about 60% to about 99%, most preferably from about 75% to about 95%) of the polymer.

Exemplary silicone-containing ionic polymers for use in the present invention include the following:

(i) acrylic acid/n-butylmethacrylate/polydimethylsiloxane (PDMS) macromer
   (ii) dimethylaminoethyl methacrylate/isobutyl methacrylate/2-ethylhexyl-methacrylate/PDMS macromer
   (iii) t-butylacrylate/acrylic acid/PDMS macromer
   (iv) t-butylacrylate/acrylic acid/PDMS macromer In one aspect of this invention the hairspray compositions comprise the hair setting resin, surfactant, and vehicle wherein the weight average molecular weight is at least about 300,000. In general, the molecular weight will be between about 300,000. and about 10,000,000, more typically from about 300,000 to about 5,000,000, preferably from about 300,000 to about 3,000,000. Enhanced benefit of resins which do not contain a silicone macromer portion, the weight average molecular weight must be at least 300,000, and can extend upward as set forth above.

In general, it is preferred not to combine cationic resins with anionic surfactants or combine anionic resins with cationic surfactants in the compositions hereof.

As is known in the art, polymers which have acidic functionalities, such as carboxyl groups, are usually used in at least partially neutralized form to promote solubility/dispersibility of the polymer. In addition, use of the neutralized form aids in the ability of the hair spray compositions to be removed from the hair by shampooing. In general, it is preferred that from about 10% to 100%, more preferably from about 20% to about 90%, even more preferably from about 40% to about 85%, of the acidic monomers of the polymer be neutralized.

Any conventionally used base, organic or metallic, may be used for neutralization of the polymers. Metallic bases are particularly useful in the present compositions. Hydroxides, where the cation is an alkali metal or an alkaline earth metal, are suitable neutralizers for use in the present hair spray compositions.

Preferred neutralizing agents for use in hair spray compositions of the present invention are potassium hydroxide and sodium hydroxide.

Examples of other suitable neturalizing agents which may be included in the hair spray compositions of the present invention include amines, especially amino alcohols such as 2-amino-2-methyl-1,3-propanediol (AMPD), 2-amine-2-ethyl-1,3-propanediol (AEPD), 2-amino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), tri-isopropanolamine (TIPA) and dimethyl steramine (DMS). Particularly useful neutralizing agents are mixtures of amines and metallic bases.

Polymers having basic functionalities, e.g., amino groups, are preferably at least partially neutralized with an acid, e.g., hydrogen chloride.

Liquid Vehicle

The hair spray compositions of the present invention also include a liquid vehicle. This can comprise any of those conventionally used in resin hair spray formulations. The liquid vehicle is present in the hair spray compositions at from about 80% to about 99%, preferably from about 85% to about 99%. More preferably, the liquid vehicle is present at from about 90% to about 98% of the total composition.

Organic solvents suitable for use in the liquid vehicle of the present compositions are $C_1$–$C_6$ alkanols, carbitol, acetone and mixtures thereof. $C_1$–$C_6$ alkanols preferred for use in the present compositions are $C_2$–$C_4$ monohydric alcohols such as ethanol, isopropanol and mixtures thereof.

Water is also suitable for use in the liquid vehicle of the present hair spray compositions.

Preferably, the liquid vehicle for the present compositions is selected from the group consisting of $C_1$–$C_6$ alkanols, water, carbitol, acetone and mixtures thereof. More preferably, the liquid vehicle of the present composition is selected from the group consisting of water and $C_2$–$C_4$ monohydric alcohols such as ethanol and isopropanol, and mixtures thereof.

In general, water may be absent from the liquid vehicle or may comprise all of the liquid vehicle. Most preferably, the liquid vehicle is a mixture of water and organic solvents.

Where water and organic solvent mixtures are used, for instance, water-ethanol or water-isopropanol-ethanol, the water content of the compositions is generally in the range of from about 0.5% to about 99%, preferably from about 5% to about 45% and most preferably from about 5% to about 20%, by weight of the total composition. In such mixtures, the organic solvents are generally present in the range of from 0% to about 99%, preferably from about 55% to about 94% and more preferably from about 80% to about 94%, by weight of the total composition.

In one aspect of the invention, the hair setting resin is of particularly high weight average molecular weight, i.e. weight average molecular weight above about 300,000, especially above about 500,000. It has been found that surprisingly effective hair spray performance can be obtained using these high molecular weight resins in combination with the surfactants, and that the surfactants are especially effective at providing the resins with characteristics in hair spray compositions such that they can be sprayed with good spray quality.

In another aspect of the invention, what is provided is a hair spray product comprising a hair spray composition in a hairspray means for containing and spraying the hair spray composition, wherein the hair spray composition is contained in the hairspray means and comprises a silicone macromer-containing ionic hair setting resin, an ionic fluorosurfactant, and a liquid vehicle, each as previously described. These compositions are further characterized by having reduced levels of volatile organic solvents. The weight average molecular weight of the silicone macromer-containing hair setting resins can be of any level suitable for providing effective hair styling. Typically, it will be at least about 50,000, more typically at least about 70,000, preferably at least about 100,000. In the more preferred embodiments of this aspect of the invention, the weight average molecular weight of the resin is from about 100,000 to about 1,000,000, more preferably from about 125,000 to about 200,000.

The use of surfactant can improve hair feel while imparting zero or a relatively minor loss in hair styling or hair hold performance. Furthermore, at higher molecular weights such as those above about 175,000, particularly those of about 200,000 and higher, improved hair feel relative to hair hold performance as well as improved spray pattern and particle size distribution can be obtained.

Although there is no absolute upper limit for molecular weight of the ionic resins other than that which may be of practical concerns, such as ability to formulate as a sprayable liquid and processing of the composition, the molecular weight will generally be less than about 10,000,000, typically less than about 5,000,000, preferably less than about 3,000,000, most preferably less than about 1,000,000.

The preferred reduced volatile organic solvent hair spray compositions of the present invention comprise the ionic, silicone macromer-containing hair setting resin surfactant, and no more than 80% volatile organic solvents (which include, for purposes hereof, volatile silicone fluids and exclude water). It is also specifically contemplated that the hair spray compositions can comprise no more than 55% volatile organic solvents, or other levels as may be chosen by product formulators or as a result of regulations. In the reduced volatile organic solvent hair spray products hereof, the hair spray compositions comprise at least 10%, by weight, of water. It is also specifically contemplated that the compositions can contain at least about 11%, 12%, 13%, 14%, 15%, or more water.

As used herein, volatile organic solvents means solvents which have at least one carbon atom and exhibit a vapor pressure of greater than 0.1 mm Hg at 20° C.

Such reduced volatile organic solvent hair spray compositions hereof utilizing non-silicone macromer-containing resins will comprise up to about 90% water, preferably up to about 70% water, most preferably up to about 60% water and most preferably no more than about 50% water. Such compositions will also contain from about 10% to about 80% of volatile organic solvents, preferably from about 20% to about 80%, even more preferably from about 40% to about 80%. It is also specifically contemplated that the compositions can contain no more than other lower maximum limits of volatile organic solvents, eg., no more than about 75%, 65%, or 55%, etc.

The level of surfactant to be used, in general, is given above. It is to be recognized, however, that the particular level of surfactant which must be used to achieve an improvement in hair spray performance, or to achieve optimum performance, for a particular hair spray composition can vary depending upon a variety of factors, including the particular type of resin chosen and its molecular weight, and level in the composition, the specific surfactant, the level of water and the type and level of volatile organic solvent, and the presence of optional components in the system. In general, higher levels of surfactant may be needed to achieve a performance benefit as resin molecular weight and/or water levels are reduced. In general, the compositions hereof should contain at least an effective amount of surfactant to provide an improvement in hair feel for a given level of hair hold performance or for improved spray quality.

Ionic Fluorinated Surfactants

Optionally, the compositions can contain ionic fluorohydrocarbon surfactants, alternately referred to as ionic fluorinated surfactants. If used, they will typically be present in the hair spray compositions of the present invention in the range of from about 0.01% to about 2%, preferably from about 0.01% to about 1.5% and more preferably from about 0.01% to about 1%.

Fluorosurfactants (i.e., fluorinated surfactants) useful in the present compositions can be linear or branched alkyl, alkenyl or alkylaryl fluorohydrocarbons having a chain length of preferably 3 to 18 carbon atoms and being fully or partially fluorinated. The hydrophilic moiety can be, for example, sulfate, phosphate, phosphonate, sulfonate, amine, amine salts, quaternary ammonium, carboxylate, and any combination thereof. Also, there can be a bridging moiety between the hydrophilic and hydrophobic moieties, such as an amido alkalene group for example.

Ionic fluorosurfactants useful in the present compositions include perfluorinated compounds represented by the formula $$CF_3-(CF_2)_x-(CH_2)_y-Z$$

where Z is a water solubilizing group of either organic or inorganic character, x is an integer which is generally from 2 to 17, particularly from 7 to 11, and y is an integer from 0 to 4, and said compounds may be cationic, anionic, amphoteric or zwitterionic, depending upon the nature of the grouping or groupings encompassed by Z. The Z groups may be or may comprise sulfate, sulfonate, carboxylate, amine salt, quaternary ammonium, phosphate, phosphonate, and combinations thereof. The perfluorinated compounds are known in the art. These compounds are described in U.S. Pat. No. 4,176,176, Cella et al., issued Nov. 27, 1979; U.S. Pat. No. 3,993,745, Cella et al., issued Nov. 23, 1976, and U.S. Pat. No. 3,993,744, Cella et al., issued Nov. 23, 1976, each being incorporated herein by reference.

Cationic fluorosurfactants preferred for use in the present compositions include fluorinated alkyl quaternary ammonium salts having a variety of anionic counter ions, including iodide, chloride, methosulfate, phosphate, and nitrate salts, preferably an iodide; and those fluorosurfactants conforming to the formula $R_fCH_2CH_2SCH_2CH_2N^+(CH_3)_3$ $[CH_3SO_4]^-$ wherein $R_f=F(CF_2CF_2)_{3-8}$, such as ZONYL FSC supplied by E. I. DuPont deNemours and Company (Wilmington, Del., USA; DuPont). A preferred fluorinated alkyl quaternary ammonium iodide is FLUORAD FC-135 supplied by Minnesota Mining & Manufacturing (St. Paul, Minn., USA; 3M).

Anionic fluorosurfactants preferred for use in the present compositions are mono-, and bis-perfluoroalkyl phosphates, such as ZONYL FSP supplied by DuPont and conforming to the general formulae $(R_fCH_2CH_2O)P(O)(ONH_4)_2$ $(R_fCH_2CH_2O)_2P(O)$ $(ONH_4)$ wherein $R_f=F(CF_2CF_2)_{3-8}$; mono- and bis-fluoroalkyl phosphates, having a variety of cationic counterions such as ammonium, sodium, potassium, triethanolamine and diethanolamine salts, preferably ammonium salts, complexed with non-fluorinated quats, preferably aliphatic quaternary methosulfates, such as ZONYL FSJ supplied by DuPont; perfluoroalkyl sulfonic acid having a variety of cationic counterions such as ammonium, sodium, potassium, triethanolamine and diethanolamine salts, preferably ammonium salts, such as ZONYL TBS supplied by DuPont and conforming to the formula $R_fCH_2CH_2SO_3X$ wherein $R_f=F(CF_2CF_2)_{3-8}$ and X=H or $NH_4$; telomer phosphates, having a variety of cationic counterions such as ammonium, sodium, potassium, triethanolamine and diethanolamine salts, preferably diethanolamine salts, such as ZONYL RP supplied by DuPont; amine perfluoroalkyl sulfonates, such as FLUORAD FC-99 supplied by 3M; ammonium perfluoroalkyl sulfonates, such as FLUORAD FC-93, FLUORAD FC-120 and L-12402, supplied by 3M; potassium perfluoroalkyl sulfonates, such as FLUORAD-95 and FLUORAD FC-98 supplied by 3M; potassium fluorinated alkyl carboxylates, such as FLUORAD FC-129 and FLUORAD FC-109 supplied by 3M; ammonium perfluoroalkyl carboxylates, such as Fluorad FC-143® supplied by 3M; and those fluorosurfactants conforming to the general formula $R_fCH_2CH_2SCH_2CH_2CO_2Li$ wherein $R_f=F(CF_2CF_2)_{3-8}$, such as ZONYL FSA supplied by DuPont.

Preferred anionic fluorosurfactants are mixed mono- and bis-perfluoroalkyl phosphates, ammonium salts; mixed mono- and bis-fluoroalkyl phosphate, ammonium salts, complexed with aliphatic quaternary methosulfates; perfluoroalkyl sulfonic acid, ammonium salts; mixed telomer phosphate diethanolamine salts; amine perfluoroalkyl sulfonates; ammonium perfluoroalkyl sulfonates; potassium perfluoroalkyl sulfonates; potassium fluorinated alkyl carboxylates; ammonium perfluoroalkyl sulfonates; and ammonium perfluoroalkyl carboxylates.

Amphoteric fluorosurfactants preferred for use in the present compositions are fluorinated alkyl amphoteric surfactants available commercially as FLUORAD FC-100 from 3M.

Zwitterionic fluorosurfactants preferred for use in the present compositions are those fluorosurfactants conforming to the formula $R_fCH_2CH(OCOCH_3)CH_2N^+(CH_3)_2CH_2CO_2^-$ wherein $R_f=F(CF_2CF_2)_{3-8}$ such as ZONYL FSK supplied by DuPont.

Preferably, mixtures of amphoteric or zwitterionic fluorosurfactants with anionic fluorosurfactants or mixtures of anionic and cationic fluorosurfactants are used.

The ionic fluorosurfactants are typically utilized at levels of from about 0.01% to about 2%, preferably from about 0.01% to about 1.5%. Most preferred is a level of from about 0.01% to about 1%.

Ionic Strength Modifier System

Optionally, the hair spray compositions of the present invention can contain an effective amount of a nonsurface active ionic strength modifier system for reducing the viscosity of the hair spray composition, relative to the same composition absent the ionic strength modifiers. When used, the present compositions will generally comprise at least about 0.01%, by weight, of the ionic strength modifier. As will be understood by those skilled in the art, as the ionic strength of the composition is increased, the resin will eventually fall out of solution, or otherwise no longer remain solubilized or dispersed in the liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Generally, the compositions will comprise about 4%, by weight, or less of the ionic strength modifiers, more generally about 2% or less, and typically about 1% or less. Preferably, the compositions hereof will comprise from about 0.01% to about 0.5%, more preferably from about 0.01% to about 0.1%, of the ionic strength modifier system.

The ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm². Generally, the ions of the ionic strength modifier system hereof will be characterized by having, at maximum, four or less carbon atoms per charge, preferably two or less carbon atoms, in any aliphatic chain or straight or branched chain organic heterochain.

The ionic strength modifier system comprises monomeric ions of the type which are products of acid-base reactions. Thus, basic and acidic ions OH⁻ and H⁺ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Suitable cations for use include, for example, alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, particularly sodium and potassium. Suitable means of addition to the compositions hereof include, for example, addition as bases, eg., hydroxides, sodium hydroxide and potassium hydroxide, and such as salts that are soluble in the liquid carrier, eg. salts of monomeric anions such as those described below.

Other suitable cations include organic ions, such as quaternary ammonium ions and cationic amines, such as ammonium mono-, di-, and tri-ethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, eg., sodium or potassium salts of acetate, citrate, nitrate, chloride, sulfate, etc. Preferably, such salts are entirely soluble in the vehicle.

Hair Spray Compositions

Hair spray compositions of the present invention can be dispensed from containers which are aerosol dispensers or pump spray dispensers. Such dispensers, i.e., containers, are well known to those skilled in the art and are commercially available from a variety of manufacturers, including American National Can Corp. and Continental Can Corp.

When the hair spray compositions are to be dispensed from a pressurized aerosol container, a propellant which consists of one or more of the conventionally-known aerosol propellants may be used to propel the compositions. A suitable propellant for use can be generally any liquifiable gas conventionally used for aerosol containers.

Suitable propellants for use are volatile hydrocarbon propellants which can include liquefied lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide and atmospheric gas.

The hydrocarbons, particularly isobutane, used singly or admixed with other hydrocarbons are preferred.

The aerosol propellant may be mixed with the present compositions and the amount of propellant to be mixed is governed by normal factors well known in the aerosol art. Generally, for liquefiable propellants, the level of propellant is from about 10% to about 60% by weight of the total composition, preferably from about 15% to about 50% by weight of the total composition.

Alternatively, pressurized aerosol dispensers can be used where the propellant is separated from contact with the hair spray composition such as a two compartment can of the type sold under the tradename SEPRO from Americal National Can Corp.

Other suitable aerosol dispensers are those characterized by the propellant being compressed air which can be filled into the dispenser by means of a pump or equivalent device prior to use. Such dispensers are described in U.S. Pat. Nos. 4,077,441, Mar. 7, 1978, Olofsson and 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use are also currently marketed by The Procter & Gamble Company under their tradename VIDAL SASSOON AIRSPRAY® hair sprays.

Conventional non-aerosol pump spray dispensers, i.e., atomizers, can also be used.

The hair spray formulations of the present invention can optionally contain conventional hair spray adjuvants. Generally, adjuvants collectively can comprise from about 0.05% to about 5% by weight and preferably from about 0.1% to about 3%, by weight. Such conventional optional adjuvants are well known to those skilled in the art and include plasticizers; silicones; emollients; lubricants and penetrants such as various lanolin compounds; protein hydrolysates and other protein derivatives; ethylene adducts and polyoxyethylene cholesterol; dyes, tints and other colorants; sunscreens; and perfume.

METHOD OF MAKING

The hair spray compositions of the present invention can be made using conventional formulation and mixing techniques. Preferably, a premix of surfactant and water is made before addition. If water is not to be used in the composition, a premix of the surfactant with an organic solvent, such as ethanol, is preferred. Methods of making hair spray compositions of the present invention are described more specifically in the following examples.

METHOD OF USE

The hair spray compositions of the present invention are used in conventional ways to provide the hair styling/holding benefits of the present invention. Such method generally involves application of an effective amount of the product to dry and/or slightly damp hair before and/or after the hair is styled. By "effective amount" is meant an amount sufficient to provide the hair hold and style benefits desired considering the length and texture of the hair. Use of the compositions of the present invention in this manner provides optimum hair holding while exhibiting good sprayability.

The following Examples further illustrate the preferred embodiments within the scope of the present invention. The Examples are given solely for the purposes of illustration and are not to be construed as limitations of the present invention as many variations of the invention are possible without departing from its spirit and scope.

EXAMPLE I

A hair spray composition of the present invention which is suitable for use in pump spray dispensers is prepared as follows:

| Ingredient | Weight % |
|---|---|
| Ethanol, 200 proof | 89.70% |
| Resin[1] | 2.50% |
| KOH (45%)[2] | 0.62% |
| DRO Water[3] | 7.00% |
| Ammonium Laureth Sulfate (28%)[4] | 0.18% |

[1]60% t-butyl acrylate/20% acrylic acid/20% silicone macromer having an average molecular weight (MW) = 10,000, having a weight average molecular weight of about 800,000.
[2]Potassium hydroxide solution containing 45% potassium hydroxide and 55% water and minors, supplied by Fisher Scientific.
[3]Double reverse osmosis water.
[4]Ammonium laureth sulfate solution containing 28% ammonium laureth (3.0) sulfate and 72% water and minors, supplied by Stepan.

The hair spray formulation of Example I is prepared by preparing a premix of the resin in isopropanol. The isopropanol premix is then added to the ethanol and then neutralized with the potassium hydroxide solution. Then, a premix of the surfactant and water is prepared and added to the neutralized premix. Other adjuvants, such as fragrances may then be added. A magnetic or air driven stirrer is used to mix the ingredients until the resin is dissolved, typically about 1 to 2 hours.

EXAMPLE II

A hair spray composition of the present invention which is suitable for use in pump spray dispensers is prepared as follows:

| Ingredient | Weight % |
|---|---|
| Ethanol, 200 proof | 79.16% |
| Isopropanol | 10.40% |
| Resin[1] | 2.60% |
| KOH (45%) | 0.69% |
| DRO Water | 7.00% |
| Ammonium laureth (3.0) Sulfate (28%) | 0.09% |
| Amphoteric-2 (40%)[2] | 0.06% |

[1]60% t-butyl acrylate/20% acrylic acid/20% silicone macromer average mw = 10,000, having a weight average molecular weight of about 1,700,000.
[2]40% cocoamphocarboxyglycinate and 60% water and minors.

The hair spray formulation of Example II is prepared by preparing a premix of the resin in ethanol. The ethanol premix is then added to the ethanol and then neutralized with the potassium hydroxide solution. Then, a premix of the surfactant and water is prepared and added to the neutralized premix. Other adjuvants, such as fragrances may then be added. A magnetic or air driven stirrer is used to mix the ingredients until the resin is dissolved, typically about 1 to 2 hours.

EXAMPLE III

A hair spray composition of the present invention which is suitable for use in pump spray dispensers is prepared as follows:

| Ingredient | Weight % |
|---|---|
| Ethanol, 200 proof | 68.87% |
| Isopropanol | 10.00% |
| Resin[1] | 3.00% |
| KOH (45%) | 0.88% |

| Ingredient | Weight % |
|---|---|
| DRO Water | 17.00% |
| Amphoteric-2 (40%) | 0.25% |

[1] 60% t-butyl acrylate/20% acrylic acid/20% silicone macromer average mw = 10,000, having a weight average molecular weight of about 690,000.

The composition is prepared as in Example II.

EXAMPLE IV

A hair spray composition of the present invention which is suitable for use in pump spray dispensers is prepared as follows:

| Ingredient | Weight % |
|---|---|
| Ethanol, 200 proof | 79.00% |
| Resin[1] | 4.00% |
| KOH (45%) | 0.82% |
| DRO Water | 15.08% |
| Aerosol OT[2] | 0.50% |

[1] 60% t-butyl acrylate/20% acrylic acid/20% silicone macromer average mw = 10,000, having a weight average molecular weight of about 500,000.
[2] Aerosol OT ®, sodium diioctylsulfosuccinate surfactant available as a 75% active solution in water and ethanol from American Cyanamid.

The composition is prepared as in Example I.

EXAMPLE V

A hair spray composition of the present invention which is suitable for use in pump spray dispensers is prepared as follows:

| Ingredient | Weight % |
|---|---|
| Ethanol, 200 proof | 19.27% |
| Resin[1] | 3.00% |
| KOH (45%) | 0.44% |
| DRO Water | 17.00% |
| Cocobetaine (35%)[2] | 0.29% |

[1] 80% t-butyl acrylate/10% acrylic acid/10% silicone macromer average mw = 10,000, having a weight average molecular weight of about 690,000.
[2] Monateric CB ®, supplied by Mona, containing 35% cocobetaine and 65% water and minors.

The composition is prepared as in Example I.

EXAMPLE VI

A hair spray composition of the present invention which is suitable for use in pump spray dispensers is prepared as follows:

| Ingredient | Weight % |
|---|---|
| Ethanol, 200 proof | 69.73% |
| Isopropanol | 10.00% |
| Resin[1] | 3.00% |
| KOH (45%) | 0.17% |
| DRO Water | 17.00% |
| Span 80/Tween 80 blend[2] | 0.10% |

[1] 70% n-butyl methacrylate/10% styrene sulfonate/20% silicone macromer average mw = 5,000, having a weight average molecular weight of about 690,000.
[2] A 95/5 blend of the nonionic organic surfactants Sorbiton Oleate and Polysorbate 80, having an average HLB of bout 4.9.

The composition is prepared as in Example II.

EXAMPLE VII

A hair spray composition of the present invention which is suitable for use in pump spray dispensers is prepared as follows:

| Ingredient | Weight % |
|---|---|
| Ethanol, 200 proof | 68.98% |
| Isopropanol | 10.00% |
| Resin[1] | 3.00% |
| KOH (45%) | 0.88% |
| DRO Water | 17.00% |
| Adogen-432 CG ® (70%)[2] | 0.14% |

[1] 75% ethyl methacrylate/20% acrylic acid/5% silicone macromer average mw = 10,000, having a weight average molecular weight of about 690,000.
[2] Contains 70% dicetyldimonium chloride and 30% water and minors, supplied by Sherex.

The composition is prepared as in Example II.

EXAMPLE VIIII

A hair spray composition of the present invention which is suitable for use in pump spray dispensers is prepared as follows:

| Ingredient | Weight % |
|---|---|
| Ethanol, 200 proof | 78.79% |
| Resin[1] | 3.00% |
| KOH (45%) | 0.88% |
| DRO Water | 17.00% |
| AMMONYX-LO ® (30%)[2] | 0.33% |

[1] 60% t-butyl acrylate/20% acrylic acid/20% silicone macromer average mw = 10,000, having a weight average molecular weight of about 690,000.
[2] AMMONYX-LO ®, supplied by Stepan contains 30% lauryl amine oxide and 70% water and minors.

The composition is prepared as in Example I.

EXAMPLE IX

A hair spray composition of the present invention which is suitable for use in pump spray dispensers is prepared as follows:

| Ingredient | Weight % |
|---|---|
| Ethanol, 200 proof | 82.10% |
| Isopropanol | 8.00% |
| Resin[1] | 2.00% |
| KOH (45%) | 0.59% |
| DRO Water | 7.00% |
| Ammonium laureth (3.0) Sulfate (28%) | 0.18% |
| Amphoteric-2 (40%) | 0.13% |

[1] 60% t-butyl acrylate/20% acrylic acid/20% silicone macromer average mw = 10,000, having a weight average molecular weight of about 1,300,000.

The composition is prepared as in Example II.

EXAMPLE X

A formulation for an aerosol hair spray concentrate is shown below. The concentrate is preferably charged with a organic propellant at about 30% propellant and 70% concentrate.

| Ingredient | Weight % |
|---|---|
| Ethanol, 200 proof | 96.38% |
| Resin[1] | 3.00% |

-continued

| Ingredient | Weight % |
|---|---|
| AMP[2] | 0.37% |
| Amphoteric-2 (40%) | 0.25% |

[1] 60% t-butylacrylate/20% acrylic acid/20% silicone macromer average mw = 10,000, having a weight average molecular weight of about 690,000.
[2] Aminomethyl propanol.

The composition is prepared as in Example I except that the premix is prepared using ethanol instead of isopropanol and the neutrualizing agent is AMP instead of the potassium hydroxide solution.

EXAMPLE XI

A hair spray composition of the present invention which is suitable for use in pump spray dispensers is prepared as follows:

| Ingredient | Weight % |
|---|---|
| Ethanol, 200 proof | 79.53% |
| Resin[1] | 2.20% |
| KOH (45%) | 0.37% |
| DRO Water | 17.00% |
| Ammonium laureth (3.0) Sulfate (28%) | 0.30% |
| Fluorad FC-100 ® (25%)[2] | 0.40% |
| Fragrance | 0.20% |

[1] 60%/t-butyl acrylate/20% acrylic acid/20% silicone macromer average mw = 10,000, having a weight average molecular weight of about 800,000.
[2] Fluorad FC-100 ®, supplied by 3M, containing 25% mixed ammonium perfluoroalkyl sulfonates, 37.5% ethanol and 37.5% water and minors.

The composition is prepared as in Example II. The fluorosurfactant is premixed along with the organic surfactants.

EXAMPLE XII

A hair spray composition of the present invention which is suitable for use in pump spray dispensers is prepared as follows:

| Ingredient | Weight % |
|---|---|
| Ethanol, 200 proof | 70.73% |
| Isopropanol | 8.80% |
| Resin[1] | 2.20% |
| KOH (45%) | 0.37% |
| DRO Water | 17.00% |
| Ammonium laureth (3.0) Sulfate (28%) | 0.30% |
| Zonyl FSK ® (47%)[2] | 0.40% |
| Fragrance | 0.20% |

[1] 60%/t-butyl acrylate/20% acrylic acid/20% silicone macromer average mw = 10,000, having a weight average molecular weight of about 800,000.
[2] Zone FSK ®, supplied by 3M, containing 47% fluorosurfactants conforming to the general formula $R_fCH_2CH(OCOCH_3)CH_2N^+—(CH_3)_2CH_2CO_2$ wherein $R_f={F(CH_2CF_2)_{3-8}}$ and 53% acetic acid and minors.

The composition is prepared as in Example XII.

EXAMPLE XIII

A hair spray composition of the present invention is prepared as follows:

| Ingredient | Weight % |
|---|---|
| Ethanol, 200 proof | 79.93% |
| Resin[1] | 5.00% |
| KOH (45%) | 0.82% |
| Aerosol OT | 0.25% |
| DRO Water | 15.00% |

[1] 60% t-butyl acrylate/20% acrylic acid/20% silicone macromer, having a weight average molecular weight of about 150,000.

The composition is prepared as in Example I. It is suitable for conventional pump spray as well as compressed air aerosol spray containers.

All of the above compositions exhibit good sprayability and, when applied to the hair, provide good hold.

In the above examples and the compositions hereof utilizing silicone macromer-grafted styling resins, the resin can be purified by removing unreacted silicone-containing monomer and silicone macromer-grafted polymer with viscosities at 25° C. of about 10,000,000 centistokes and less. This can be done, for the example, by hexane extraction. After drying the resin from its reaction solvent, hexane extraction of the reaction product can be performed by adding an excess of hexane to the reaction product and heating to near the Tg of the non-silicone portion of the polymer. The mixture is held at this temperature with stirring for about 30 minutes and cooled to room temperature. The hexane is removed by vacuum suction. Two more hexane extraction cycles are preferably conducted in the same manner as above. After the third cycle, residual hexane remaining with the product is removed by distillation and vacuum drying.

What is claimed is:

1. A hairspray product comprising a liquid, sprayable hairspray composition and a spray dispenser means for containing and spraying said hairspray composition, said hairspray composition being contained in said spray dispenser means, wherein said hairspray composition comprises:

(a) from about 0.01% to about 2%, by weight, of a non-fluorinated surfactant selected from the group consisting of ionic surfactants, nonionic surfactants having an hydrophilic lipophilic balance of about 7 or less and mixtures thereof;

(b) from about 0.1% to about 15%, by weight of a silicone macromer-containing hair setting resin having an organic polymeric backbone wherein the silicone-containing resin is ionic and comprises from about 0.01% to about 50% of a silicone-containing monomer having the formula:

$$X(Y)_nSi(R)_{3-m}Z_m$$

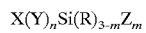

wherein X is a vinyl group copolymerizable with the other monomers of the polymer; Y is a divalent linking group; R is a hydrogen, hydroxyl, lower $C_1$–$C_4$ alkyl, aryl, alkylamino, alkaryl, or alkoxy; Z is a monovalent siloxane polymeric moiety having a number average molecular weight of at least about 500, and is pendant from the organic polymeric backbone; n is 0 or 1; and m is an integer from 1 to 3; and (c) a liquid vehicle comprising a mixture of water and an organic solvent,
wherein said composition comprises at least about 10%, by weight, water and at least about 40%. by weight of the organic solvent.

2. A hairspray product as in claim 1 wherein said resin has a weight average molecular weight of at least about 70,000.

3. A hairspray product as in claim 2, wherein said resin has a weight average molecular weight of from about 100,000 to about 1,000,000.

4. A hairspray product as in claim 3, wherein said resin has a weight average molecular weight of from about 125,000 to about 200,000.

5. A hairspray product as in claim 1, wherein said silicone-containing ionic resin comprises from about 2% to about 75%, by weight of said silicone-containing ionic resin, of an ionic monomer and from about 25% to about 98%, by weight of said silicone-containing ionic resin, of a nonionic monomer, and wherein said silicone-containing ionic resin contains at least about 0.5%, by weight of said silicone-containing monomer.

6. A hairspray product as in claim 5, wherein said ionic monomer is acrylic acid, methacrylic acid, dimethylaminoethyl methacrylate, quaternized dimethylamino methacrylate, maleic acid, half esters of maleic anhydride, crotonic acid, itaconic acid, diallyldimethyl ammonium chloride, vinyl pyridine, vinyl imidazole, styrene sulfonate, or a mixture thereof.

7. A hairspray product as in claim 6, wherein said nonionic monomer is selected from the group consisting of acrylic acid esters of $C_1$–$C_{24}$ alcohols, methacrylic acid esters of $C_1$–$C_{24}$ alcohols, styrene, polystyrene macromer, vinyl acetate, vinyl chloride, vinyl propionate, vinylidene chloride, alphamethylstyrene, t-butylstyrene, butadiene, cyclohexadiene, ethylene, propylene, vinyl toluene, and mixtures thereof.

8. A hairspray product as in claim 7, wherein said resin comprises silicone-macromer containing monomer having the formula:

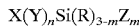

wherein X is a vinyl group; Y is a divalent linking group; R is a hydrogen, lower alkyl, aryl or alkoxy; Z is a monovalent siloxane polymeric moiety having a number average molecular weight of at least about 500; n is 0 or 1; and m is an integer from 1 to 3.

9. A hairspray product as in claim 8, wherein said surfactant is selected from the group consisting of:
1) alkyl sulfates, alkyl ether sulfates, olefin sulfonates, alkyl sulfonates, sulfosuccinimates, β-alkyloxy alkane sulfonates;
2) alkyl amphoglycinates, alkyl amphosulfonates, alkyl amphopropionates, alkyl amphosulfosuccinimates;
3) alkyl betaines, alkyl amido betaines, alkyl amino sulfonates, sulfo betaines; and 4) mixtures thereof.

10. A hairspray product as in claim 1, wherein said spray dispenser means is an aerosol spray container.

11. A hair spray product as in claim 10, further comprising an aerosol propellant disposed within said container.

12. A hair spray product as in claim 11, wherein said aerosol spray container is a pump spray container, wherein compressed air is utilized as a propellant.

13. A hair spray product as in claim 1, wherein said means for containing and spraying said composition is a nonaerosol pump spray container.

14. A hair spray product as in claim 1, wherein said composition comprises from about 11% to about 60% water.

15. A hair spray product as in claim 14, wherein said composition comprises from about 13% to about 50% water.

16. A hair spray product as in claim 15, wherein said composition comprises from about 14% to about 50% water.

17. A method for providing hair setting benefits to the hair, comprising spraying an effective amount of the composition of claim 1 to hair wherein the amount is sufficient to provide a desired hair hold and style.

18. A method for providing hair setting benefits to the hair, comprising spraying an effective amount of the composition of claim 8 to hair wherein the amount is sufficient to provide a desired hair hold and style.

19. A liquid hair spray composition as in claim 1, wherein said silicone macromer-containing monomer is:

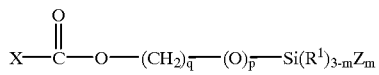

wherein m is 1, 2, or 3, p is 0 or 1, R is a hydrogen, hydroxyl, C1–C4 alkyl, aryl, alkylamino, alkaryl, or alkoxy, q is an integer from 2 to 6, X is:

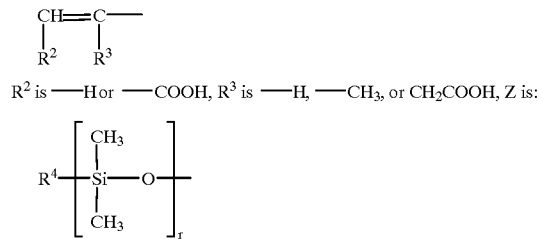

wherein $R^4$ is alkyl, alkoxy, alkylamino, aryl, alkaryl, hydrogen or hydroxyl, and r is an integer of at least about 5.

20. A hairspray product as in claim 1, wherein said organic solvent is selected from the group consisting of $C_1$–$C_6$ alkanols, carbitol, acetone, and mixtures thereof.

* * * * *